United States Patent [19]

Drake

[11] 3,948,989
[45] Apr. 6, 1976

[54] N-MONOSUBSTITUTED AMIDE PRODUCTION

[75] Inventor: Charles A. Drake, Bartlesville, Okla.

[73] Assignee: Phillips Petroleum Company, Bartlesville, Okla.

[22] Filed: June 12, 1974

[21] Appl. No.: 478,536

[52] U.S. Cl. .......................... 260/561 N; 260/561 R
[51] Int. Cl.² ...................................... C07C 103/08
[58] Field of Search ......... 260/561 N, 669 R, 465.9, 260/561 R

[56] References Cited
UNITED STATES PATENTS

| | | | |
|---|---|---|---|
| 3,013,066 | 12/1961 | Alderson ...................... | 260/465.8 D |
| 3,479,392 | 11/1969 | Stern et al. ...................... | 260/497 A |
| 3,527,794 | 9/1970 | Heck ............................... | 260/669 R |
| 3,564,007 | 2/1971 | Stern et al. ...................... | 260/561 N |
| 3,595,901 | 7/1971 | Smith ............................... | 260/465.9 |
| 3,674,884 | 7/1972 | Moritani et al. ................. | 260/669 R |
| 3,689,583 | 9/1972 | Kominami et al. .............. | 260/669 R |
| 3,752,839 | 8/1973 | Drinkard et al. ................ | 260/465.9 |
| 3,775,511 | 11/1973 | Shue ............................... | 260/669 R |

*Primary Examiner*—C. Davis

[57] ABSTRACT

N-monosubstituted amides are prepared from nitriles and either olefinically unsaturated hydrocarbons or secondary or tertiary alcohols in the presence of a group VIII metal catalyst. The amides produced by the process of this invention are useful as solvents, organic synthesis intermediates, pesticides, cationic surface active agents, etc.

7 Claims, No Drawings

N-MONOSUBSTITUTED AMIDE PRODUCTION

This invention relates to the production of N-monosubstituted amides. In another aspect, this invention relates to a process for the production of N-monosubstituted amides by the reaction of nitriles with olefinic reactants in the presence of a group VIII metal catalyst. In accordance with a further aspect, this invention relates to the production of N-monosubstituted amides by the reaction of nitriles with secondary or tertiary alcohols in the presence of a group VIII metal catalyst.

In the preparation of amides by employing the Ritter reaction, in which a suitable nitrile and a suitable olefin are reacted in the presence of materials such as strong sulfuric acid, it is frequently difficult to control the reaction temperature and extensive efforts are usually required in order to insure the control of the dangerous exotherm resulting from such a reaction. In addition, neutralization of these acids requires large amounts of base and produces large amounts of water and salts which require extensive treatment in a plant. The present invention simplifies the workup procedure considerably. The instant invention provides a less vigorous and hence more easily controlled reaction which can be safely conducted in conventional equipment. Also, in the known procedures for the preparation of amides, the processes have sometimes resulted in poor yields of the desired product.

Accordingly, an object of this invention is to provide a process for the production of N-monosubstituted amides. Another object of this invention is to provide a process yielding a high percentage of N-monosubstituted amides.

A further object of this invention is to provide an economically feasible process for the production of N-monosubstituted amides.

Other aspects, objects, and the several advantages of the invention will be apparent to those skilled in the art from a study of this disclosure and the appended claims.

In accordance with the present invention, N-monosubstitued amides are prepared by the reaction of nitriles with either olefinic reactants or secondary or tertiary alcohols in the presence of a catalyst comprising a compound of a group VIII metal with atomic number 44 or larger.

In accordance with a specific embodiment of the invention, N-tert.-butyl acrylamide is produced in good yields by the reaction of a nitrile, such as acrylonitrile, with an olefinic reactant, such as isobutylene, in the presence of a palladium halide catalyst.

In accordance with another specific embodiment of the invention, N-tert.-butyl acrylamide is produced by the reaction of acrylonitrile as the nitrile with a tertiary alcohol, such as t-butanol, in the presence of a palladium halide catalyst.

Olefinic reactants which can be used to produce N-monosubstituted amides of this invention can be represented by the formula $$R_2'C=CR_2'$$

wherein each R' group can be hydrogen, aliphatic hydrocarbon, cycloaliphatic hydrocarbon and the like, and can be alike or different and the total number of carbon atoms in the olefinic reactant can range from 3 to about 20 carbon atoms per molecule. The olefinic reactant can contain more than one ethylenically unsaturated site per molecule and any or all such sites can react with the nitrile as shown herein below. Gem-disubstituted olefinic reactants constitute a preferred class of olefins for use in this invention. Examples of some olefins which can be employed in the process include propylene, isobutylene, 2-methyl-1-butene, 1,5-octadiene, 2-cyclohexyl-2-pentene, 1-eicosene, and the like.

Secondary or tertiary alcohol reactants which can be employed according to the invention have the formula $$R_3''COH$$

wherein R'' is selected from hydrogen, alkyl, cycloalkyl, and combinations thereof and the R'' groups may be either alike or different. The total number of carbon atoms in the alcohol molecule can range from 3 to about 20 carbon atoms. Examples of some alcohols which can be employed in the process include isopropanol, tert.-butanol, 3-ethyl-3-hexanol, 3-cyclohexyl-3-octanol, 2-eicosanol, etc.

Nitrile compounds that can be reacted according to the invention have the formula $$R(CN)_x$$

wherein R is selected from aliphatic and cycloaliphatic radicals, and the total number of carbon atoms in the nitrile molecule range from 2 to about 20 carbon atoms, and wherein x is an integer of 1 to 6. It is understood that suitable nitriles for this invention can contain more than one nitrile group per molecule in which case any or all of the nitrile group can react as set forth herein below. Examples of some nitriles which can be employed in the process include acetonitrile, propionitrile, acrylonitrile, adiponitrile, cyanocyclohexane, eicosonitrile and the like.

Thus, in actual operation the preparation of N-monosubstituted amides from nitriles and olefins is exemplified by the following reaction:

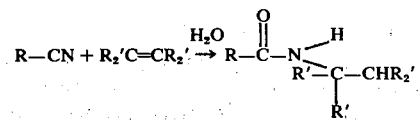

In another embodiment, N-monosubstituted amides prepared from nitriles and secondary or tertiary alcohols can be exemplified by the following reaction:

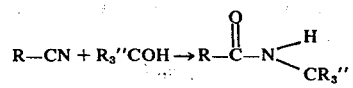

The alcohols or olefinic reactants are generally used with the nitriles in amounts ranging from 0.1 to 10 parts by weight of alcohol or olefin per part by weight of nitrile.

Catalysts for the reaction are selected from compounds of the following Group VIII metals, ruthenium, rhodium, palladium, osmium, iridium, and platinum. Compounds of these metals which are useful are the oxides, halides, nitrates, sulfates, etc. Palladium chloride is preferred. The amount of catalyst required in the reaction generally ranges from 0.1 to 5 parts by weight per one hundred parts by weight of total reactants.

Reaction temperature usually depends on the reactivity of the reactants, but it will normally be within the range 125°–225°C. Reaction time depends on the desired degree of reaction, reactivity of reactants and temperature. Reaction times of several minutes to ten hours or more are generally satisfactory. Reactions may be run at autogenous pressure, but it is frequently desirable to pressure the reactor with an inert diluent gas to a pressure of up to 1000 psi.

The amides produced by the process are useful as solvents, organic synthesis intermediates, pesticides, cationic surface active agents, etc.

EXAMPLE I

In a one liter reactor were placed acrylonitrile (40 gm), t-butanol (125 gm) and palladium chloride (3 gm). After the reactor was flushed with nitrogen, it was pressured with nitrogen to 500 psig. Heating for 2½ hours at 175°C gave a reaction mixture containing two phases. The lower phase, containing water, was discarded while the upper organic phase was retained for the workup. The organic phase was combined with those obtained by repeating the reaction three times using a total of 180 gm acrylonitrile, 525 gm isobutylene and 11 gm palladium chloride and three hours reaction time at 175°C. Distillation of the combined products showed 35 percent of acrylonitrile converted to product of which 46 percent was N-tert.-butyl acrylamide (m.p. 124°–129°C).

EXAMPLE II

In a 100 ml reactor were placed acrylonitrile (15 gm), water (5 gm) and palladium chloride (0.5 gm). After the reactor was flushed with nitrogen, isobutylene (12 gm) was added. Heating to 150°C for one hour converted 30 percent of acrylonitrile to products of which 40 percent was N-tert.-butyl acrylamide. Conversion and yield were estimated from glc analysis of crude reaction mixture.

I claim:

1. A process for preparing N-monosubstituted amides comprising reacting ethylenically unsaturated hydrocarbons having from 3 to about 20 carbon atoms and water or secondary or tertiary alcohols containing from 3 to about 20 carbon atoms with a nitrile having from 2 to about 20 carbon atoms in the presence of a catalyst comprising a compound of a Group VIII metal having an atomic number of 44 and greater.

2. A process according to claim 1 wherein the ethylenically unsaturated hydrocarbon has the formula

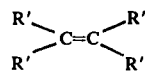

wherein R' is selected from hydrogen, aliphatic and cycloaliphatic radicals and wherein the total molecule contains from 3 to about 20 carbon atoms, the nitrile has the formula $R(CN)_x$ wherein R is selected from aliphatic and cycloaliphatic radicals and the total number of carbon atoms in the nitrile molecule ranges from 2 to about 20 carbon atoms and $x$ is an integer of 1 to 6, and the N-monosubstituted amide product has the formula

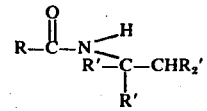

wherein R and R' are as defined.

3. A process according to claim 1 wherein the secondary or tertiary alcohol has the formula $R_3''COH$ wherein R'' is selected from hydrogen, alkyl and cycloalkyl radicals and wherein the total molecule contains from 3 to about 20 carbon atoms, the nitrile has the formula $R(CN)_x$ wherein R is selected from aliphatic and cycloaliphatic radicals and the total number of carbon atoms in the nitrile molecule ranges from 2 to about 20 carbon atoms and $x$ is an integer of 1 to 6, and the N-monosubstituted amide has the formula

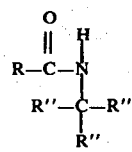

wherein R and R'' are as defined.

4. A process according to claim 1 wherein said catalyst is a compound of ruthenium, rhodium, palladium, osmium, iridium or platinum.

5. A process according to claim 1 wherein the amount of alcohol or ethylenically unsaturated hydrocarbon ranges from 0.1 to 10 parts by weight per part by weight of nitrile and the amount of catalyst present ranges from 0.1 to 5 weight parts per 100 weight parts of total reactants and the reaction temperature is in the range of 125°–225°C.

6. A process according to claim 2 for the production of N-tert.-butyl acrylamide which comprises reacting isobutylene with acrylonitrile in the presence of palladium chloride catalyst.

7. A process according to claim 3 for the production of N-tert.-butyl acrylamide which comprises reacting t-butanol with acrylonitrile in the presence of palladium chloride catalyst.

* * * * *